(12) United States Patent  (10) Patent No.: US 7,799,575 B2
Jiang  (45) Date of Patent: Sep. 21, 2010

(54) FLOW CYTOMETERS

(75) Inventor: Yonggang Jiang, New Milton (GB)

(73) Assignee: Genetix Limited, Hampshire (GB)

( * ) Notice: Subject to any disclaimer, the term of this patent is extended or adjusted under 35 U.S.C. 154(b) by 988 days.

(21) Appl. No.: 11/593,582

(22) Filed: Nov. 7, 2006

(65) Prior Publication Data

US 2008/0108146 A1  May 8, 2008

(51) Int. Cl.
*G01N 21/64* (2006.01)
*G01N 21/05* (2006.01)

(52) U.S. Cl. .............................. 436/165; 436/8; 436/63; 436/164; 436/172; 436/180; 422/82.05; 422/82.08; 73/1.01; 73/1.02

(58) Field of Classification Search ............... 436/8, 436/10, 63, 164, 165, 172, 180; 422/73, 422/82.05, 82.08; 73/1.01, 1.02, 1.03
See application file for complete search history.

(56) References Cited

U.S. PATENT DOCUMENTS

| 5,084,394 | A | * | 1/1992 | Vogt et al. | 436/8 |
| 5,093,234 | A | * | 3/1992 | Schwartz | 435/7.21 |
| 6,542,833 | B1 | * | 4/2003 | Nygaard | 702/46 |
| 2003/0078703 | A1 | * | 4/2003 | Potts et al. | 701/1 |
| 2005/0030519 | A1 | * | 2/2005 | Roth | 356/28.5 |

FOREIGN PATENT DOCUMENTS

EP  1 666 857 A1  6/2006

OTHER PUBLICATIONS

Kraan et al., "Setting up and Calibration of a Flow Cytometer for Multicolor Immunophenotyping," *Journ, of Biological Regulators and Homeostatic Agents*, 2003, vol. 17, pp. 223-233.
Morilla et al., "Quantitiative Flow Cytometery", vol. 33/4 Proceedings RMS Dec. 1998, pp. 267-270.
Morgan et al., "Production of Precise Microbiology Standards Using Flow Cytometry and Freeze Drying," *Cytometry Part A*, vol. 62A, pp. 162-168, 2004.
Hamamatsu Brochure for H9530, Jul. 2004, 15 pages.
Hamamatsu Preliminary Data for H9530, Oct. 2004, 2 pages.
Hamamatsu Brochure Extract for H9797R/H9797T, 2006, 1 page.

* cited by examiner

*Primary Examiner*—Maureen M Wallenhorst
(74) *Attorney, Agent, or Firm*—Foley & Lardner LLP (57) ABSTRACT

A calibration method for a flow cytometer with a multichannel detector module. During calibration, the fluorescence intensity data values for the different detector channels are used to calculate normalization factors needed to adjust subsequent data collected by each of the channels. By using a multichannel detector module, the results from the different flow cells can be reliably compared, so that multiple stages of flow cells can be arranged in series along a common flow path, for example to measure the same sample at defined time intervals.

16 Claims, 5 Drawing Sheets

FLOW CYTOMETERS

BACKGROUND OF THE INVENTION

The invention relates to flow cytometers and to methods of calibrating and using flow cytometers.

Flow cytometers are widely used for analysing properties of cells that are suspended in a liquid. The liquid is passed through a conduit so that the cells flow past a fluorescence-based sensing device one at a time. The cells can thus be counted and classified according to their spectroscopic properties which can then optionally be used to further direct the flow or for other purposes. For example, the cells can be sorted downstream of the detection device according to their fluorescence properties. This is usually referred to as fluorescence activated cell sorting (FACS).

The instrument typically is provided with multiple detectors to collect both forward and side scattered light from the cells. Side scatter (SSC) refers to an orthogonal, or at least transverse, alignment of the optical axes of the excitation and collection optics. Forward scatter (FSC) refers to a transmission mode optical set up. A typical machine will have one detector arranged for forward scatter collection and several detectors arranged for side scatter collection. Usually fluorescence data at different emission wavelengths are collected by multiple detectors arranged in side scatter. As well as for cell counting, the instrument is sensitive to a variety of cell properties, such as size, morphology, membrane roughness, granularity of the cytoplasm and many others. Generally each cell type has a unique combination of measured properties, including fluorescence, and correlation of FSC and SSC signals, which allow the cell type of each cell to be identified. Moreover, healthy and diseased cells of the same type may be distinguishable.

Before using a flow cytometer to measure fluorescence signals from cell samples marked with fluorescent tags, it is first necessary to calibrate the system so that the absolute intensity of the fluorescence signal measured by each combination of excitation source and detector is known. Otherwise, for example, test results from different instruments cannot be compared and results from one day to the next cannot be compared.

One necessary aspect of calibration of the instrument is to quantify the amount of fluorescence that is measured at each emission band or channel of interest. Each excitation/emission combination can thus be ascribed a calibration value with which measured data needs to be scaled. These calibration values can be represented in a calibration curve as a function of emission wavelength, for example. Now, assuming the source, detector, intervening optics, and other parameters are not changed, the signals obtained from a subsequent sample can have their fluorescence intensities quantified by scaling the measured values with the appropriate calibration values. The number of fluorescence molecules per cell, or whatever other parameter is being measured, can then be reliably calculated.

In this respect it is noted that the detectors used are typically photomultiplier tubes (PMTs) and these are well known for having sensitivity that changes over time, in particular from session to session. This is inherent in their design being essentially high voltage biased vacuum tubes operating at or near breakdown with avalanching effects. However, PMTs are difficult to displace with other detectors in view of their extremely high sensitivity.

A separate PMT may be used for each wavelength channel. On the other hand, it is also known to use multichannel PMTs where each channel receives a different wavelength band. The company Hamamatsu markets such a multichannel PMT under product numbers H9530 and H9797 series. This product integrates an 8-channel PMT with an input side optical arrangement of dichroic mirrors to spectrally sort an input beam into the 8-channels. A full technical description of this product is provided in EP 1 666 857 A1 [1] as well as in Hamamatsu product literature which refers to the suitability of this product for flow cytometers, cell sorters, cell analyzers, laser scanning microscopy and other specified uses.

For these reasons calibration is a major concern when using a flow cytometer. The typical approaches are to perform calibration runs with calibration beads and/or to run test experiments with standard samples of known and reproducible fluorescence properties.

Figure 1:
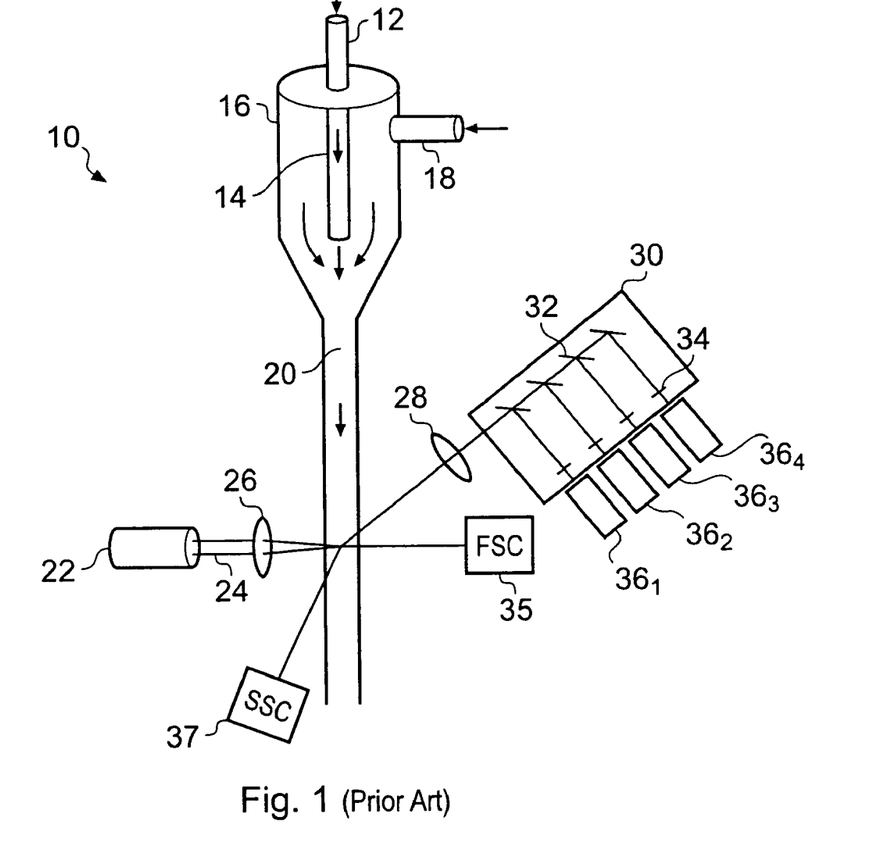
FIG. 1 shows schematically the flow cell region of a conventional flow cytometer.

FIG. 1 shows schematically the flow cell region of a conventional flow cytometer using multiple PMTs. The flow cytometer has a flow cell 10 which receives a sample inlet tube 12. The sample inlet tube 12 is connected to an inner capillary tube 14 of the flow cell 10 which is radially enclosed prior to its termination by a sheath 16 which has a sheath inlet 18 connected to a sheath fluid inlet tube (not shown). As considered in the flow direction, the sheath 16 reduces in its cross-sectional diameter and the inner capillary tube 14 terminates leaving the sample fluid and sheath fluid flowing together along a capillary tube 20. After this termination, the sample flows radially confined to the central region of the flow by virtue of laminar flow at the interface between the sample fluid and the sheath fluid. The aim of this sheath arrangement is to allow good optical access to the sample in a flow tube that is sufficiently large in diameter to avoid blockages.

The various optical components for excitation and collection are arranged about a measurement region of the capillary tube 20. A laser 22 outputs a laser beam 24 that is focused by a lens 26 on the central region of the capillary tube 20 so as to intersect with the sample. Fluorescence from the sample excited by the laser 22 is then collected through a collection lens 28 and spectral sorting arrangement 30, comprising mirrors 32 and filters 34, which divides the fluorescence into different wavelength bands. Each color component is directed to a suitable PMT $36_1$, $36_2$, $36_3$, $36_4$ as illustrated with the example of four PMTs. A FSC detector 35 and SSC detector 37 may also be provided and are schematically depicted. Moreover, although not illustrated, multiple lasers may be provided to cover all excitation wavelengths of interest. Also, the laser or lasers may be tuneable.

Figure 2:
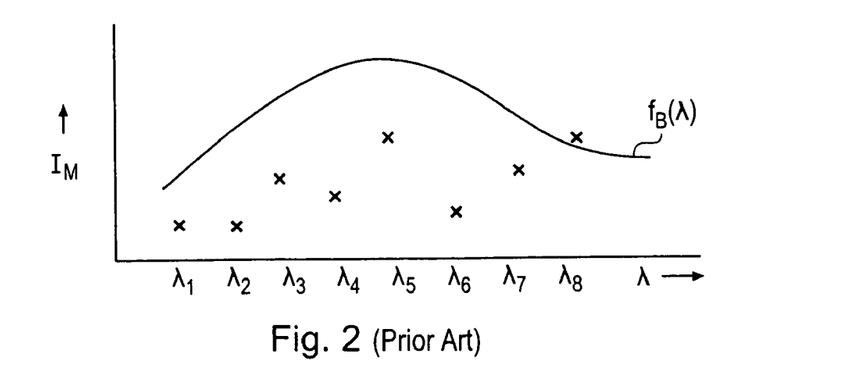
FIG. 2 is a graph showing schematically aspects of a conventional calibration process.

FIG. 2 is a graph showing schematically aspects of a conventional calibration process for an 8-channel detector assembly using 8 PMTs. The channels cover respective wavelength bands centered at $\lambda_1, \lambda_2, \lambda_3, \lambda_4, \lambda_5, \lambda_6, \lambda_7, \lambda_8$, wherein these wavelengths will generally be unevenly spaced and centered on a particular emission band of interest. A standard calibration method is now described. A set of broadband fluorescent calibration beads is supplied to the instrument to acquire calibration data on each of the 8 channels. The respective measured intensities for the channels are illustrated by the crosses in the figure and have values $I_c(\lambda_i)$ where i=1 to 8. Optionally some blank beads may also be run to obtain a zero baseline intensity $I_0$. In the illustrated example, no baseline is shown. The calibration beads have a known spectral response $f_B(\lambda)$ as plotted in the figure. In the illustrated example, it can thus be seen that generally the measured intensities $\lambda_1$ to $\lambda_7$ are lower than they should be, but $\lambda_8$ is approximately correct. Each of the channels is then normalized according to the strength of the measured signal taking account of the calibration bead response, namely the normalization factor $N_i$ for each channel is given by the equation:

$$N_i = c \cdot \frac{f_B(\lambda_i)}{I_C(\lambda_i) - I_0}$$

where c is an arbitrary constant. The normalization factors are then used in subsequent measurements to adjust the measured intensities $I_M$ according to the formula, so that a processed intensity $I_P$ is arrived at by the formula $I_P = N_i \cdot I_M$. The measured intensities of samples of interest are thus adjusted to take account of the measured intensities for the calibration beads.

Each wavelength channel is thus normalized according to its sensitivity. This information is typically stored in software. This is a standard approach along similar principles to what is discussed throughout the literature on flow cytometry, for example see the references [2, 3, 4].

SUMMARY OF THE INVENTION

The invention provides a method of calibrating a flow cytometer, the method comprising: providing a flow cell through which a sample to be studied flows and a fluorescence detection assembly comprising a spectral sorting arrangement for separating fluorescence extending over a wavelength range into a plurality of at least four wavelength bands, and a single detector module with a plurality of channels to which the spectral sorting arrangement is optically coupled so that respective channels thereof receive respective ones of the wavelength bands; flowing a fluorescent calibration sample through the flow cell which fluoresces across the wavelength range; measuring the intensity of the fluorescent calibration sample in each of the channels of the detector; and determining normalization factors for each channel from a known spectral response function for the fluorescent calibration sample and the measured intensities of the fluorescent calibration sample, the normalization factors being suitable for adjusting subsequent measured fluorescence intensities of samples to be investigated.

The calibration method of the invention takes advantage of the multichannel nature of the detector which means that the channel-to-channel sensitivity variations should be predictable and also vary collectively over time as a result of for example fluctuations in a common bias voltage, since data from all the channels are collected simultaneously.

The general high level of accuracy of the calibration method is important in practice not only since the data collected are more accurate, but also since re-calibration need not be carried out so frequently.

Advantageously, the method may further comprise: flowing a control sample through the flow cell which is substantially not fluorescent across the wavelength range; and measuring the intensity of the control sample in each of the channels of the detector; wherein the normalization factors are determined also from the measured intensities of the control sample.

The method may also further comprise: flowing a further fluorescent calibration sample through the flow cell which fluoresces across the wavelength range; and measuring the intensity of the further fluorescent calibration sample in each of the detector channels; wherein the normalization factors are determined also from the measured intensities of the further fluorescent calibration sample by solving first and second simultaneous equations corresponding respectively to the fluorescent calibration sample and the further fluorescent calibration sample.

The invention further includes a method of measuring the fluorescence of a sample in a flow cytometer, the method comprising: calibrating the flow cytometer according to the invention as specified above; flowing a sample to be investigated through the flow cell; measuring the fluorescence intensity of the sample in each of the detector channels; and normalizing the fluorescence intensity measured in each channel according to the normalization factor for that channel.

The invention further provides a flow cytometer having a data processing unit operable to perform the calibration method and/or method of measuring the fluorescence of a sample according to the invention as described above.

The calibration process of the invention allows the results from the different flow cells to be reliably compared. In turn this allows a flow cytometer to be provided according to the invention that comprises a plurality of measurement units arranged along a common flow path through which a sample to be studied flows, thereby flowing passed each measurement unit in turn, wherein each measurement unit comprises a flow cell, and wherein each flow cell is arranged in optical communication with a fluorescence detection assembly comprising a spectral sorting arrangement for separating fluorescence extending over a wavelength range into a plurality of at least four wavelength bands, and a single detector module with a plurality of channels to which the spectral sorting arrangement is optically coupled so that respective channels thereof receive respective ones of the wavelength bands.

A common optical excitation source, typically a laser, can be shared between the different units and split using beam splitters or optical fibers, for example. Alternatively each unit can be given a dedicated optical source. Similarly, the flow cells can be arranged in optical communication with their own fluorescence detection assemblies, or by an optical multiplexing arrangement, all of the flow cells, or groups of them, can share a fluorescence detection assembly.

The invention still further provides a method of measuring the fluorescence of a sample in a flow cytometer, comprising a plurality of measurement units arranged along a common flow path through which a sample to be studied flows, thereby flowing passed each measurement unit in turn, wherein each measurement unit comprises a flow cell, and wherein each flow cell is arranged in optical communication with a fluorescence detection assembly comprising a spectral sorting arrangement for separating fluorescence extending over a wavelength range into a plurality of at least four wavelength bands, and a single detector module with a plurality of channels to which the spectral sorting arrangement is optically coupled so that respective channels thereof receive respective ones of the wavelength bands, the method comprising: flowing a sample to be investigated through the flow path; and measuring the fluorescence intensity of the sample in each of the measurement units in turn.

BRIEF DESCRIPTION OF THE DRAWINGS

For a better understanding of the invention and to show how the same may be carried into effect reference is now made by way of example to the accompanying drawings.

DETAILED DESCRIPTION

Figure 3:
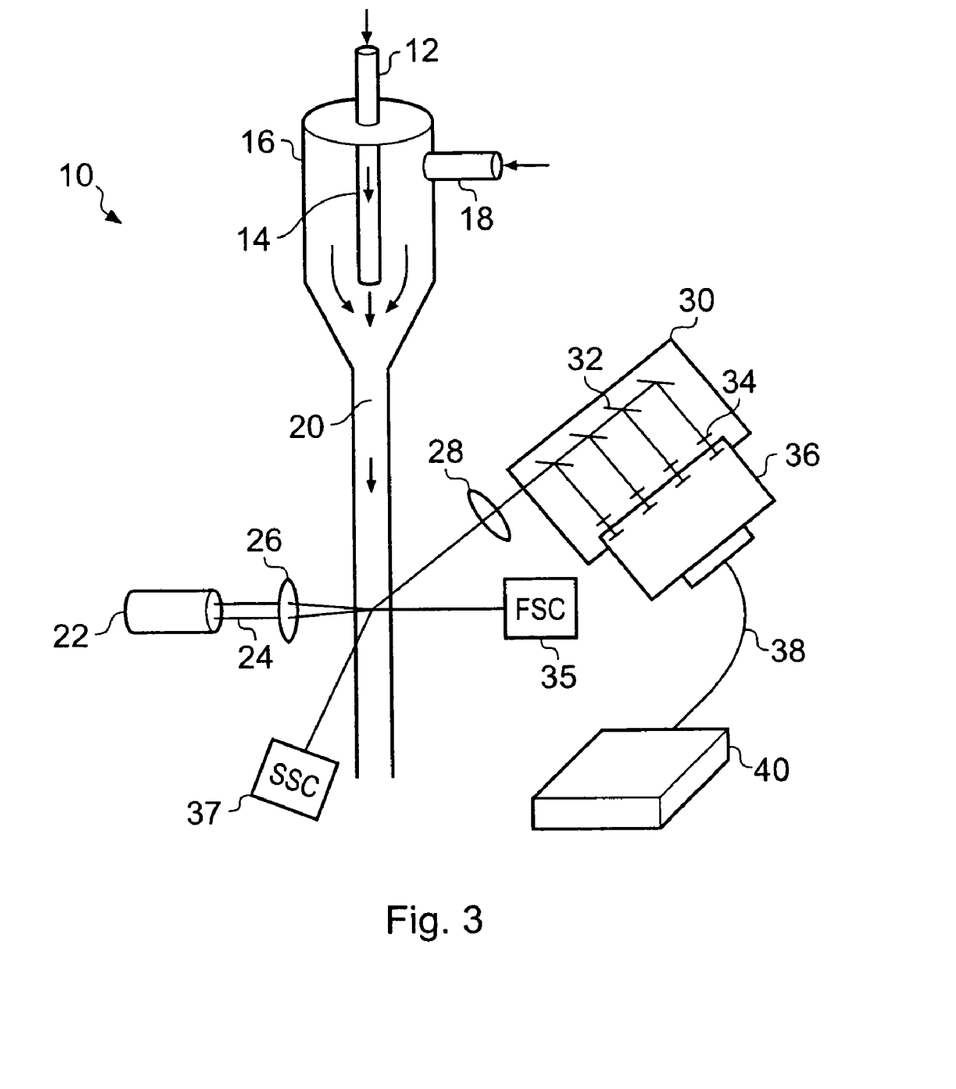
FIG. 3 shows schematically the flow cell region of a flow cytometer embodying the invention.

FIG. 3 shows schematically the flow cell region of a flow cytometer embodying the invention. The apparatus is similar in many respects to the prior art apparatus shown in FIG. 1 and the same reference numerals are used for corresponding parts.

Namely, the flow cytometer has a flow cell 10 which receives a sample inlet tube 12. The sample inlet tube 12 is connected to an inner capillary tube 14 of the flow cell 10 which is radially enclosed prior to its termination by a sheath 16 which has a sheath inlet 18 connected to a sheath fluid inlet tube (not shown). As considered in the flow direction, the sheath 16 reduces in its cross-sectional diameter and the inner capillary tube 14 terminates leaving the sample fluid and sheath fluid flowing together along a capillary tube 20. After this termination, the sample flows radially confined to the central region of the flow through laminar flow being preserved at the interface between the sample fluid and the sheath fluid. The aim of this sheath arrangement is to allow good optical access to the sample in a flow tube that is sufficiently large in diameter to avoid blockages.

The various optical components for excitation and collection are arranged about a measurement region of the capillary tube 20. A laser 22 outputs a laser beam 24 that is focused by a lens 26 on the central region of the capillary tube 20 so as to intersect with the sample. Suitable laser types and wavelengths are by way of example gas lasers, such as Argon ion lasers (e.g. 488 nm, 502 nm, 514 nm) or Krypton ion lasers (530 nm, 568 nm, 647 nm), or Helium-Neon lasers (e.g. 633 nm). Tuneable lasers may also be used, such as dye lasers. Light emitting diodes (LEDs) may also be used.

Fluorescence from the sample excited by the laser 22 is then collected through a collection lens 28 and spectral sorting arrangement 30 comprising mirrors 32 and filters 34 which divide the fluorescence into different wavelength bands. A FSC detector 35 and SSC detector 37 may also be provided and are schematically depicted.

Each fluorescence component is directed to a suitable channel of a single integral detector in the form of a multichannel PMT 36. The spectral sorter and PMT assembly is of the Hamamatsu series 9530 which has 8-channels (not 4 as illustrated for convenience). In general, it is noted that many other numbers of channels could be used, with 4 being the practical minimum. The maximum number of wavelength channels would not be expected to exceed 16-20. An FSC detector may also be provided, but is not shown. Moreover, although not illustrated, multiple lasers may be provided to cover all excitation wavelengths of interest. Also, the laser or lasers may be tuneable. The PMT 36 is connected through a communication line 38 to a data processing unit 40, which may be a personal computer or dedicated electronics unit. The data processing unit 40 is used to perform the calibration process of the invention and to subsequently acquire and pre-process data from samples of interest.

Since all channels are from a single PMT 36 with a common bias, the multichannel nature of the detector means that the channel-to-channel sensitivity fluctuate collectively over time as a result of for example fluctuations in the common bias voltage, since data from all the channels are collected simultaneously. This means that calibration of the detector will be reliable for a relatively long period in comparison to a situation in which separate, individually biased, PMTs are used for each channel.

Figure 4:
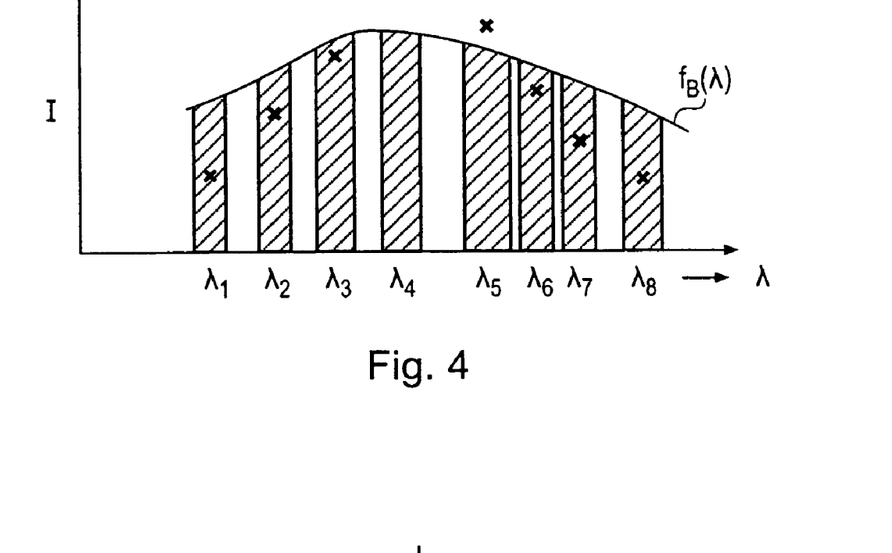
FIG. 4 show a graph according to a calibration process embodying the invention.

FIG. 4 is a graph showing schematically a calibration process embodying the invention for the 8-channel detector assembly with wavelength bands centered at $\lambda_1, \lambda_2, \lambda_3, \lambda_4, \lambda_5, \lambda_6, \lambda_7, \lambda_8$, wherein these wavelengths will generally be unevenly spaced and of different widths $\Delta\lambda_i$ where $i=1$ to 8, with each band centered on a particular emission band of interest. Typically the bands will be sorted by appropriate filters or other wavelength selecting optical components. The bands are illustrated schematically in the graph by the hatched columns. The sensitivity range of the detector is approximately in the range 300-850 nm for the Hamamatsu series 9530 detector.

A set of broadband fluorescent calibration beads is supplied to the instrument to acquire some calibration data on each of the 8 channels, the intensities of which are illustrated by the crosses in the figure and have values $I_C(\lambda_i)$ where $i=1$ to 8. The calibration beads have a known spectral response $f_B(\lambda)$ as plotted in the figure.

The calibration process takes account of the varying widths of the detector channels by incorporating integration across each band according to the formula:

$$F_i(B, \lambda) = \int_{\lambda_i - \Delta\lambda_i/2}^{\lambda_i + \Delta\lambda_i/2} f_B(\lambda) d\lambda$$

To calculate $F_i(B, \lambda)$ the known spectral response $f_B(\lambda)$ of the calibration sample is used as well as the different channel widths by integrating between $\lambda_i - \Delta\lambda_i/2$ and $\lambda_i + \Delta\lambda_i/2$ for each channel. The normalisation factors $N_i$ then follow by dividing $F_i(B, \lambda)$ by $I_{\lambda,i}$ as shown by the formula:

$$N_i = c \cdot \frac{F_i(B, \lambda)}{I_C(\lambda_i) - f_0(\lambda_i)}$$

where $f_0(\lambda_i)$ is a base intensity obtained from a run of blank (i.e. non-fluorescent) beads and c is an arbitrary constant. The normalization factors are then used in subsequent measurements to adjust the measured intensities $I_M$ according to the formula, so that a processed intensity $I_P$ is arrived at by the formula $I_P = N_i \cdot I_M$. The measured intensities of samples of interest are thus adjusted to take account of the measured intensities for the fluorescent calibration beads and also optionally the blank beads.

Figure 5:
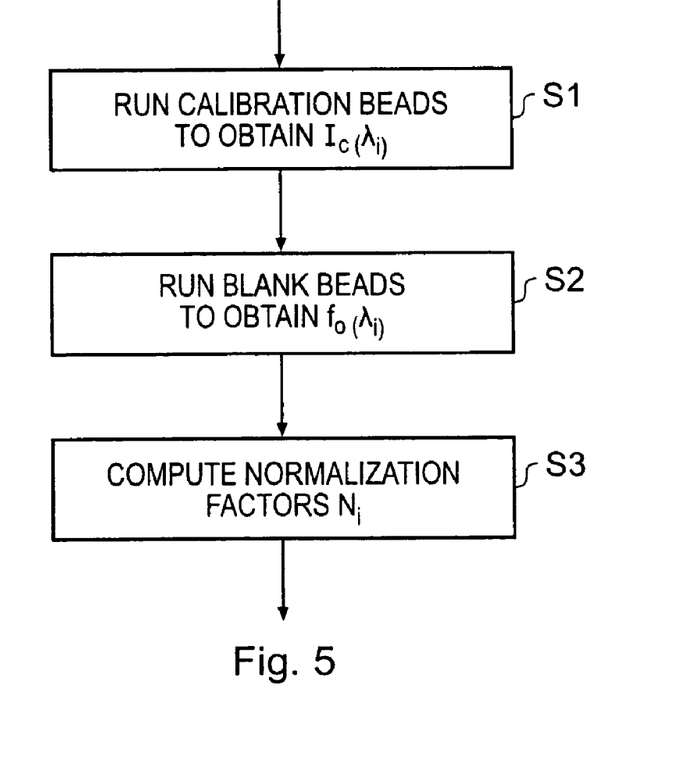
FIG. 5 is a flow diagram of the calibration process of FIG. 4.

FIG. 5 is a flow diagram of the calibration process.

In Step S1, a run with calibration beads is made and a set of intensity data values $I_C(\lambda_i)$ for each of the channels is acquired.

In Step S2, a run with blank beads is made and a set of intensity data values $f_0(\lambda_i)$ for each of the channels is acquired.

In Step S3, the intensity data for each channel are normalized for the known wavelength dependence of the bead response and taking account of the blank bead response to compute the normalization factors $N_i$.

The calibration is then complete, and measurements on samples of interest can be made and adjusted using the calculated normalization factors. It is noted that the background signal $f_0(\lambda_i)$ from the blank bead run may be substantially constant for all wavelengths, may have a substantially linear rise or fall across the wavelength range, or may have some more complex functional form.

Figure 6A:
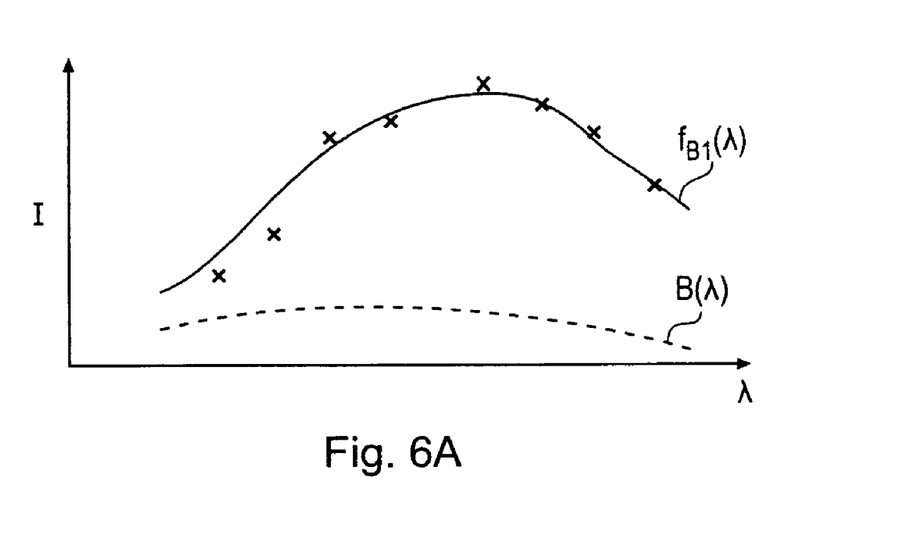
FIGS. 6A and 6B are graphs according to a further calibration process embodying the invention.
Figure 6B:
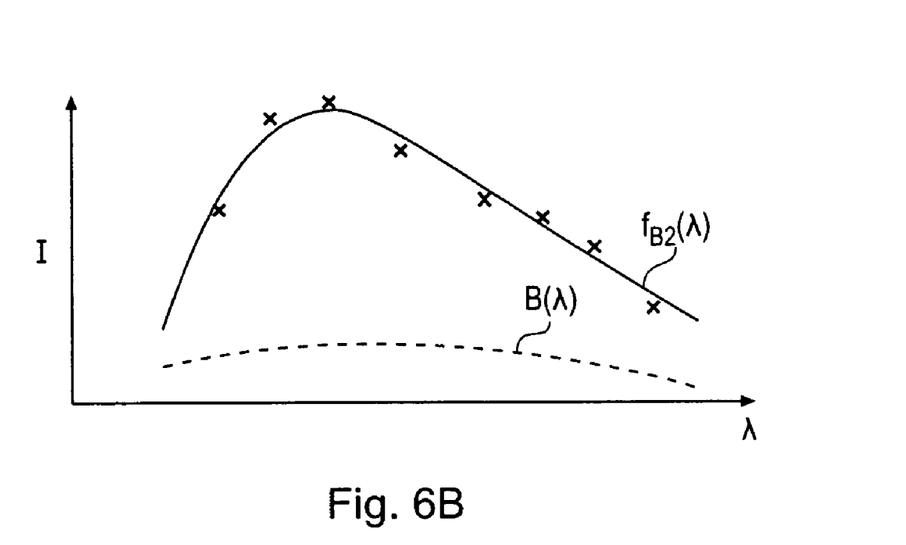

FIGS. 6A and 6B show graphs according to a further calibration process embodying the invention. This example is predicated on the assumption that the apparatus will have an intrinsic, but unknown, background fluorescence $B(\lambda)$ which will be the same regardless of the calibration sample. Such a sample-independent background can be numerically removed by carrying out two separate calibration runs with two known calibration samples, such as beads, of different known responses $f_{B1}(\lambda)$ and $f_{B2}(\lambda)$. In the figure, example intensity data for the two calibration runs is illustrated with the two graphs, where similar annotations and symbol conventions are used as above. The unknown background fluorescence $B(\lambda)$ is illustrated by the dashed line in both graphs. Running the two calibration processes in parallel allows the background fluorescence $B(\lambda)$ to be determined, and thus taken account of, using the two simultaneous equations set up by the duplicate calibration process, namely:

$$N_i = c \cdot \frac{F_i(B_1, \lambda)}{I_{C1}(\lambda_i) - B(\lambda)}, N_i = c \cdot \frac{F_i(B_2, \lambda)}{I_{C2}(\lambda_i) - B(\lambda)}$$

Solving these two equations simultaneously allows determination of the normalization factors $N_i$ as well as the background $B(\lambda)$, where the normalization factors are thus free of the background.

Figure 7:
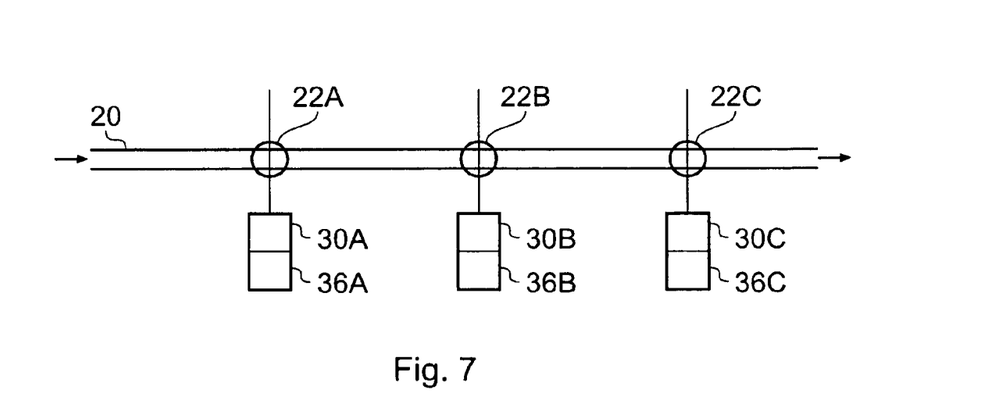
FIG. 7 is a schematic drawing of a multi-stage flow cytometer according to the invention.

FIG. 7 is a schematic drawing of a multi-stage flow cytometer according to the invention. In this embodiment, the instrument comprises a plurality of flow cells $10_i$ arranged in series along a capillary tube 20, so that the flow cells $10_i$ each measure a given sample one after the other as the sample passes along the tube. Assuming constant flow velocity, the sample is thus measured at a series of times separated by a time interval proportional to the distance between flow cells. Accordingly, if the cells are equally spaced, the multiple measurements of a given sample occur at fixed time intervals.

Each flow cell $10_i$ is generally as described in connection with the previous embodiments. Namely, the detector assemblies $30_i/36_i$ each comprise a spectral sorting arrangement in combination with a multi-channel PMT $36_i$ as described further above together with a laser source $22_i$. The necessary further optical components previously described are also included. In the drawing, three stages A, B and C are shown by way of example, but any number of stages between 2 and perhaps 10 or 20 could be contemplated.

In use, it is thus possible to vary the time interval by varying the flow velocity by suitable adjustment of the circulation pump (not shown). With this method it is possible to measure dynamics of processes over the time scale defined by the flow velocity and unit separation. For example, the change in the fluorescence spectrum measured by the multi-channel PMTs can be measured over time to track process dynamics.

What makes this multi-stage approach practical from a technical point of view is the improved calibration process of the invention which allows the results from the different flow cells to be reliably compared. Moreover, from a commercial and engineering perspective, the use of the compact, integrated detector assemblies 30/36 of the type supplied by Hamamatsu allows a multi-stage system to be made at viable cost and manageable size.

Figure 8:
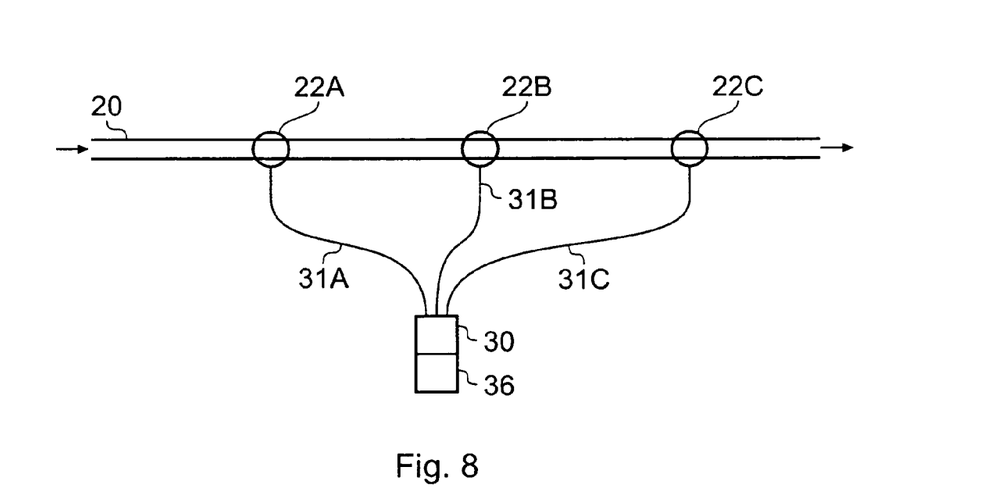
FIG. 8 is a schematic drawing of a modified multi-stage flow cytometer according to the invention.

FIG. 8 is a schematic drawing of a modified design of multi-stage flow cytometer according to the invention. In this modified design, the different stages share a common detector assembly 30/36, with each flow cell being connected to the detector assembly by suitable optical waveguiding or free space optics or a combination thereof. Suitable waveguides would be optical fibers, more especially multimode optical fibers, or light pipes. Suitable free space optics would utilize mirrors and/or lenses. In the figure optical fibers 31A, 31B and 31C are shown connecting the respective flow cells A, B and C to the detector, wherein the optical fibers are multiplexed by a suitable optical multiplexer proximal to the detector.

Another option to reduce the number of detector assemblies would be to have recirculating flow so that the sample passes the detector assemblies a multiple number of times. This option is not illustrated.

REFERENCES

[1] EP 1 666 857 A1 (Hamamatsu)
[2] Kraan, Gratama, Keeney and D'Hautcourt: "Setting up and calibration of a flow cytometer for multicolor immunophenotyping" Journal of Biological Regulators and Homeostatic Agents 2003, volume 17, pages 223-233
[3] Morilla and Scolnik "Quantitative Flow Cytometery" Volume 33/4 Proceedings RMS December 1998, pages 267-270
[4] Morgan, Bigeni, Herman, Gauci, White and Vesey "Production of Precise Microbiology Standards Using Flow Cytometry and Freeze Drying" Cytometry Part A, Volume 62A, pages 162-168 (2004)

What is claimed is:

1. A method of calibrating a flow cytometer, the method comprising:
    providing a flow cell through which a sample to be studied flows and a fluorescence detection assembly comprising a spectral sorting arrangement for separating fluorescence extending over a wavelength range into a plurality of at least four wavelength bands, and a single detector module with a plurality of channels to which the spectral sorting arrangement is optically coupled so that respective channels thereof receive respective ones of the wavelength bands;
    flowing a fluorescent calibration sample through the flow cell which fluoresces across the wavelength range;
    measuring the intensity of the fluorescent calibration sample in each of the channels of the detector; and
    determining normalization factors for each channel from a known spectral response function for the fluorescent calibration sample and the measured intensities of the fluorescent calibration sample, the normalization factors being suitable for adjusting subsequent measured fluorescence intensities of samples to be investigated, the method further comprising flowing a further fluorescent calibration sample through the flow cell which fluoresces across the wavelength range; and
    measuring the intensity of the further fluorescent calibration sample in each of the detector channels;
    wherein the normalization factors are determined also from the measured intensities of the further fluorescent calibration sample by solving first and second simultaneous equations corresponding respectively to the fluorescent calibration sample and the further fluorescent calibration sample.

2. The method of claim 1, further comprising:
    flowing a control sample through the flow cell which is substantially not fluorescent across the wavelength range; and measuring the intensity of the control sample in each of the channels of the detector;
wherein the normalization factors are determined also from the measured intensities of the control sample.

3. A method of measuring the fluorescence of a sample in a flow cytometer, the method comprising:
calibrating the flow cytometer according to claim 2;
flowing a sample to be investigated through the flow cell;
measuring the fluorescence intensity of the sample in each of the detector channels; and
normalizing the fluorescence intensity measured in each channel according to the normalization factor for that channel.

4. A method of measuring the fluorescence of a sample in a flow cytometer, the method comprising:
calibrating the flow cytometer according to claim 1;
flowing a sample to be investigated through the flow cell;
measuring the fluorescence intensity of the sample in each of the detector channels; and
normalizing the fluorescence intensity measured in each channel according to the normalization factor for that channel.

5. A flow cytometer having a data processing unit operable to measure the fluorescence of a sample according the method of claim 4.

6. A flow cytometer having a data processing unit operable to perform the calibration method of claim 1.

7. A flow cytometer comprising a plurality of measurement units arranged along a common flow path through which a sample to be studied flows, thereby flowing past each measurement unit in turn, wherein each measurement unit comprises a flow cell, and wherein each flow cell is arranged in optical communication with a fluorescence detection assembly comprising a spectral sorting arrangement for separating fluorescence extending over a wavelength range into a plurality of at least four wavelength bands, and a single detector module with a plurality of channels to which the spectral sorting arrangement is optically coupled so that respective channels thereof receive respective ones of the wavelength bands, further comprising a data processing unit operable to compare measurements of the fluorescence intensities of the sample in each of the measurement units to measure changes in the fluorescence over time.

8. A method of measuring the fluorescence of a sample in a flow cytometer, comprising a plurality of measurement units arranged along a common flow path through which a sample to be studied flows, thereby flowing past each measurement unit in turn, wherein each measurement unit comprises a flow cell, and wherein each flow cell is arranged in optical communication with a fluorescence detection assembly comprising a spectral sorting arrangement for separating fluorescence extending over a wavelength range into a plurality of at least four wavelength bands, and a single detector module with a plurality of channels to which the spectral sorting arrangement is optically coupled so that respective channels thereof receive respective ones of the wavelength bands, the method comprising:
flowing a sample to be investigated through the flow path; and
measuring the fluorescence intensity of the sample in each of the measurement units in turn, and comparing the measurements to measure changes in the fluorescence over time.

9. The method of claim 8, further comprising:
measuring the fluorescence intensity of the sample in each of the detector channels for each of the measurement units; and
normalizing the fluorescence intensity measured in each channel according to a normalization factor for that channel for each of the measurement units, wherein said normalization factors are determined by flowing a fluorescent calibration sample through the measurement units which fluoresces across the wavelength range; measuring the intensity of the fluorescent calibration sample in each of the channels for each of the measuring units; and determining the normalization factors for each channel from a known spectral response function for the fluorescent calibration sample and the measured intensities of the fluorescent calibration sample.

10. The method of claim 8, further comprising
calibrating the flow cytometer prior to flowing a sample to be investigated through the flow path, wherein the flow cytometer is calibrated by a method comprising:
flowing a fluorescent calibration sample through each of the flow cells which fluoresces across the wavelength range;
measuring the intensity of the fluorescent calibration sample for each of the flow cells in each of the channels of the detector; and
determining normalization factors for each channel for each of the flow cells from a known spectral response function for the fluorescent calibration sample and the measured intensities of the fluorescent calibration sample, the normalization factors being suitable for adjusting subsequent measured fluorescence intensities of samples to be investigated.

11. A flow cytometer having a data processing unit operable to perform the calibration procedure of claim 10.

12. The method of claim 8, further comprising
calibrating the flow cytometer prior to flowing a sample to be investigated through the flow path, wherein the flow cytometer is calibrated by a method comprising:
flowing a fluorescent calibration sample through each of the flow cells which fluoresces across the wavelength range;
measuring the intensity of the fluorescent calibration sample for each of the flow cells in each of the channels of the detector;
flowing a control sample through each of the flow cells which is substantially not fluorescent across the wavelength range; and
measuring the intensity of the control sample in each of the channels of the detector for each of the flow cells; and
determining normalization factors for each channel for each of the flow cells from a known spectral response function for the fluorescent calibration sample and the measured intensities of the fluorescent calibration sample, the normalization factors being suitable for adjusting subsequent measured fluorescence intensities of samples to be investigated,
wherein the normalization factors are determined also from the measured intensities of the control sample.

13. The method of claim 8, further comprising
calibrating the flow cytometer prior to flowing a sample to be investigated through the flow path, wherein the flow cytometer is calibrated by a method comprising:
flowing a fluorescent calibration sample through each of the flow cells which fluoresces across the wavelength range;
measuring the intensity of the fluorescent calibration sample for each of the flow cells in each of the channels of the detector;

flowing a further fluorescent calibration sample through each of the flow cells which fluoresces across the wavelength range; and measuring the intensity of the further fluorescent calibration sample for each of the flow cells in each of the detector channels;

determining normalization factors for each channel for each of the flow cells from a known spectral response function for the fluorescent calibration sample and the measured intensities of the fluorescent calibration sample, the normalization factors being suitable for adjusting subsequent measured fluorescence intensities of samples to be investigated, and wherein the normalization factors are determined also from the measured intensities of the further fluorescent calibration sample by solving first and second simultaneous equations corresponding respectively to the fluorescent calibration sample and the further fluorescent calibration sample.

14. The method of claim 8, wherein the flow cells are arranged in optical communication with respective fluorescence detection assemblies.

15. The method of claim 8, wherein the flow cells are arranged in optical communication with a shared fluorescence detection assembly.

16. A flow cytometer having a data processing unit operable to measure the fluorescence of a sample according the method of claim 8.

* * * * *